United States Patent [19]

Kim

[11] Patent Number: 4,668,798

[45] Date of Patent: May 26, 1987

[54] PROCESS FOR PREPARING PYRROLIDINE DERIVATIVES

[76] Inventor: Don K. Kim, 36-9, Kye-Dong, Chongro-ku, Seoul, Rep. of Korea

[21] Appl. No.: 793,966

[22] Filed: Nov. 1, 1985

[30] Foreign Application Priority Data

Dec. 19, 1984 [KR] Rep. of Korea ............... 84-8084[U]

[51] Int. Cl.$^4$ .................. C07C 154/00; C07D 207/08
[52] U.S. Cl. ................................. 548/533; 260/502.6
[58] Field of Search ...................... 548/533; 260/502.6

[56] References Cited

U.S. PATENT DOCUMENTS

| | | | |
|---|---|---|---|
| 4,046,889 | 9/1977 | Ondetti et al. | 548/533 X |
| 4,105,776 | 8/1978 | Ondetti et al. | 548/533 X |
| 4,297,282 | 10/1981 | Ohashi et al. | 548/533 |
| 4,332,725 | 6/1982 | Fischer et al. | 548/533 |
| 4,460,780 | 7/1984 | Ohashi et al. | 548/533 X |

OTHER PUBLICATIONS

Japan Laid-Open Patent Spec. 56-100760; (English language abstract thereof); Aug. 12, 1981.

Primary Examiner—Joseph Paul Brust
Attorney, Agent, or Firm—Watts, Hoffmann, Fisher & Heinke

[57] ABSTRACT

The present invention relates to a novel process for preparing pyrrolidine derivatives of the formula(I):

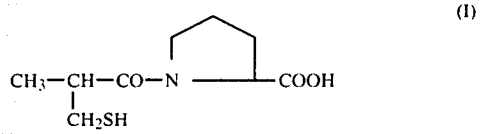

characterized in that the compound of formula(II):

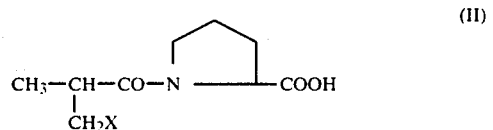

wherein, X is halogen atom such as bromo or chloro; is reacted with the aqueous solution of the compound of formula(III):

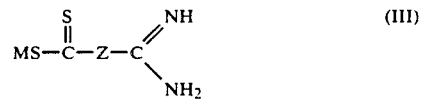

wherein,
M is alkali metal,
Z is sulfur or oxygen;
and followed by hydrolysis in the presence of an acid.

The compounds according to this invention are useful as drugs for lowering blood pressure and preventing hypertension.

10 Claims, No Drawings

PROCESS FOR PREPARING PYRROLIDINE DERIVATIVES

The present invention relates to a new process for the preparation of the compounds of formula (I) which are useful for lowering blood pressure and preventing hypertension.

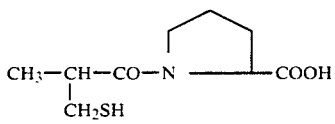

Pyrrolidine derivatives are known and can be obtained by the procedures described in U.S. Pat. No. 4,046,889. That is, the alkyl ester of 1-(3-alkylcarbonylthio-2-methylpropionyl)-L-proline is treated with anisole and trifluoroacetic acid to obtain its free acid. The free acid thus obtained is ammonoilized by reacting it with alcoholic ammonia or concentrated ammonium hydroxide solution, or hydrolized by reacting it with a solution of alkali-metal hydroxide thereby obtaining the desired 1-(3-mercapto-2-methylpropionyl)-L-proline. U.S. Pat. No. 4,297,282 describes a process for preparing the desired compounds by deacylating N-(D-α-methyl-β-acetylthiopropionyl)-L-proline with an alcoholic ammonia.

Japanese Laid-open Pat. Specification No. 56-100760 describes a process which comprises reacting 1-(3-bromo-(2S)-methylpropionyl)-pyrrolidone-(2S)-carboxylic acid with sodium thiosulfate to obtain Bunte salt and subjecting the Bunte salt to hydrolysis with hydrochloric acid to produce the desired compound. The aforementioned processes have the drawbacks that non-reduced sulfide is not easily separated but remains as impurities in the resulting product, and the production yield is not very high. The present invention eliminates these drawbacks and provides a novel and advantageous process for preparing the desired compound of formula (I).

The present invention provides a novel process for preparing the compound of formula (I) by reacting the compound of formula (II) with the compound of formula (III) and then subjecting the resulting intermediate compound to hydrolysis in the presence of an acid.

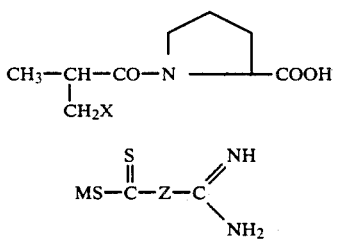

wherein
X is halogen atom such as, chloro or bromo,
M is alkali metal,
Z is oxygen or sulfur.

Further the present invention provides a novel method in which the compound of formula (III) is obtained by reacting carbon disulfide with urea or thiourea in the presence of an inorganic base solution. The base used for the preparation of the compound of formula (III) may include sodium hydroxide, potassium hydroxide, sodium carbonate, potassium carbonate and the like.

The solvent which may be used in the reaction includes water soluble organic solvents, but an aqueous solution is preferred. The reaction is carried out preferably at a temperature within the range 20° to 50° C.

The compound of formula (III) thus obtained may be used directly for the next reaction step without separating the compound of formula (III) from its aqueous solution. Still further, the present invention provides a method of producing the intermediate compound and subsequent hydrolysis of the intermediate compounds. Thus, the compound of formula (III) is reacted in an amount of 1 to 4 moles per mole of the compound of formula (II), and the reaction is carried out preferably at a temperature within the range 30° to 100° C. It is worthy of note that if the compound of formula (II) is not neutralized using a base before reacting it with the compound of formula (III), excessive consumption of the compound of formula (III) will result. The base that may be used includes for example, sodium hydrogen cabonate, potassium hydrogen carbonate, sodium carbonate, potassium carbonate, sodium hydroxide, potassium hydroxide, and the like or triethylamine, pyridine, and the like.

The reaction mixture thus obtained by reacting the compound of formula (II) and the compound of formula (III) is further subjected to hydrolysis with inorganic acid such as hydrochloric acid or sulfuric acid, or organic acid such as formic acid, and the like at a pH value ranging from 0.5 to 2.5, to give the desired compound of formula (I).

The following examples illustrate the details of this invention. However, it should be understood that they are not intended thereby to limit the scope of the present invention.

PREPARATION OF THE REACTANT (a) Preparation of sodium ureido dithiocarbonate solution.

6.06 g of urea and 4.30 g of sodium hydroxide are added to 80 ml of distilled water. While being stirred at room temperature, 18.3 ml of carbon disulfide is added drop-wise and then the solution is slowly heated to 45° C. and maintained for 6 hours at this temperature. The excess carbon disulfide is removed to obtain a transparent red solution.

(b) Preparation of sodium thioureido dithiocarbonate solution.

4.02 g of thiourea and 2.15 g of sodium hydroxide were added to 40 ml of distilled water. While stirring, 9.2 ml of carbon disulfide was added drop-wise and then the solution was heated to a temperature within the range 40° to 45° C. and reacted for 5 hours. The excess carbon disulfide was removed by vacuum distillation, and a transparent red solution was obtained.

(c) Preparation of potassium ureido dithio-carbonate solution.

3.03 g of urea and 3.30 g of potassium hydroxide were dissolved in 40 ml of distilled water. While stirring, 9.2 ml of carbon disulfide was added drop-wise and slowly heated to a temperature within the range 40° to 45° C. and maintained at this temperature for 5 hours. A transparent red solution was obtained by vacuum distillating the excess carbon disulfide.

EXAMPLE 1

5.64 g of 1-(3-bromo-2S-methylpropionyl)-pyrrolidine-2S-carboxylic acid was added to 20 ml of distilled water. While stirring, 1.68 g of sodium hydrogen carbonate and 40 ml of sodium ureido dithiocarbonate solution were added and heated to a temperature between 65° C. and 70° C. and reacted for 5 hours. The reaction mixture was adjusted to a pH value of 1.0 by adding concentrated hydrochloric acid and stirred for another 1 hour and thereafter extracted three times with 50 ml of methylene chloride each time. A yellow syrup was obtained by vacuum distillating the extract.

20 ml of 1N $H_2SO_4$ and 0.2 g of Zinc powder were added to the syrup and vigorously stirred for 2 hours at room temperature. The reaction mixture was extracted three times with 25 ml of ethyl acetate each time and thereafter washed with 30 ml of saturated sodium chloride solution, dried over magnesium sulfate and filtered. The remaining syrup after concentration by vacuum distillation was dissolved in 20 ml of ethyl acetate and subjected to filtration.

Hexane was added to the filtrate and the resulting precipitate was filtered and dried at a temperature of 40° C. overnight to obtain 4.0 g of 1-(3-mercapto-2S-methylpropionyl)-pyrrolidine-2S-carboxylic acid as white crystals.

| Melting Point: | 105° C. |
| --- | --- |
| $[\alpha]_D^{25}$: | −131.8° (c = 1.7, ethanol) |
| TLC: | Benzene:Butanol:Acetic acid = 25:3:3, Rf = 0.5 |

EXAMPLE 2

2.82 g of 1-(3-bromo-2S-methylpropionyl)-pyrrolidine-2S-carboxylic acid was added to 4 ml of distilled water. While stirring, 25 ml of sodium thioureido dithiocarbonate solution was added and reacted at a temperature ranging from 80° to 85° C. for 4 hours.

The reaction mixture was cooled to room temperature and the pH value adjusted to 1.0 by adding hydrochloric acid and then further agitated for 1 hour.

The resulting solution was extracted three times with 25 ml of ethyl acetate each time, and by concentrating the extract under reduced pressure, greenish-yellow syrup was obtained. 15 ml of 1N $H_2SO_4$ and 0.1 g of zinc powder were added to the syrup and stirred at room temperature for 2 hours.

The reaction mixture was extracted three times with 15 ml of ethyl acetate time, washed with 20 ml of saturated sodium chloride solution, and then concentrated by distillation under reduced pressure to obtain a colorless syrup. 10 ml of ethyl acetate was added to this syrup and the solution was precipitated with hexane. The precipitate was filtered and dried to obtain 1.8 g of white crystals, which are identical with those of example 1.

| Melting Point: | 104.3° C. |
| --- | --- |
| $[\alpha]_D^{25}$: | −131.5° (c = 1.7 ethanol) |
| TLC: | Benzene:Butanol:Acetic acid = 25:3:3, Rf = 0.5 |

EXAMPLE 3

Following the procedure described in Example 1, using potassium ureido dithiocarbonate solution, the product which was identical with that of example 1 was obtained.

| Melting Point: | 104.4° C. |
| --- | --- |
| $[\alpha]_D^{25}$: | −131.8° (c = 1.7, ethanol) |
| TLC: | Benzene:Butanol:Acetic acid = 25:3:3, Rf = 0.5 |

What is claimed is:

1. A method for preparing a compound of the formula

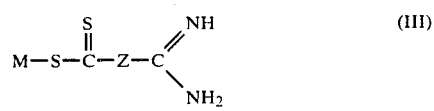

wherein M is an alkali metal and wherein Z is selected from oxygen and sulfur, by reacting carbon disulfide with a urea of the formula

in the presence of an alakli metal base in the amount of 3 moles carbon disulfide to 1 mole urea and 1 mole base at a temperature within the range of 20° to 50° C.

2. A method of preparing pyrrolidine derivatives of the formula

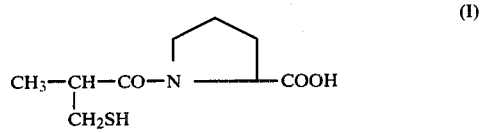

comprising the steps of:

(a) preparing a solution of a compound of the formula

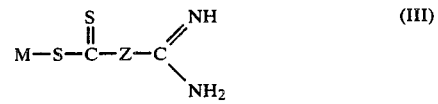

said solution being essentially free of carbon disulfide, wherein M is an alkali metal and wherein Z is selected from oxygen and sulfur, by reacting carbon disulfide with a urea of the formula

in the presence of an alkali metal base, in an amount of 3 moles of carbon disulfide to 1 mole of urea and 1 mole of said base, at a temperature with the range of 20° to 50° C.;

(b) mixing the solution from step (a) with a compound of the formula

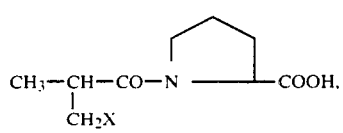
(II)

wherein X is selected from chlorine and bromine, in an amount of 1 to 4 moles of compound of formula (III) to 1 mole of compound of formula (II);

(c) heating the mixture from step (b) at a temperature within the range of 30° to 100° C. so as to displace the halogen from the compound of formula (II) with the anion of formula (III); and thereafter (d) hydrolyzing the mixture from step (c) by adjusting the pH of the mixture to a pH within the range of 0.5 to 2.5 to yield a compound of formula (I).

3. The method of claim 2 wherein step (a) is carried out for about 5 to 6 hours and wherein the alkali metal base is selected from sodium hydroxide, potassium hydroxide, sodium carbonate and potassium carbonate.

4. The method of claim 2 wherein step (b) includes the further step of neutralizing the compound of formula (II) with a basic compound in an amount of 2 moles basic compound to 3 moles compound of formula (II).

5. The method of claim 4 wherein the basic compound is selected from sodium hydrogen carbonate, potassium hydrogen carbonate, sodium carbonate, potassium carbonate sodium hydroxide, potassium hydroxide, triethylamine and pyridine.

6. The method as claimed in claim 2 wherein step (c) is carried out for about 4 to 5 hours.

7. The method as claimed in claim 2 wherein step (d) is accomplished by adding an acid selected from hydrochloric, sulfuric and formic acids and by stirring the mixture for an hour.

8. The method as claimed in claim 7 wherein step (d) includes the further step of adding acid and zinc powder in an amount of about 1 mole of a compound of formula (I) to 0.5–1 mole of acid and 0.1–0.2 mole zinc, wherein the acid is selected from sulfuric and hydrochloric acids.

9. A method of preparing pyrrolidine derivatives of the formula

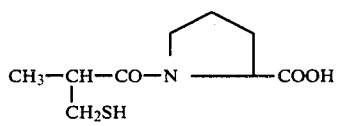
(I)

comprising the comprises of:

(a) preparing a solution of a compound of the formula

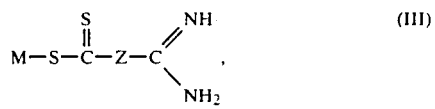
(III)

said solution being essentially free of carbon disulfide, wherein M is selected from sodium and potassium and wherein Z is selected from oxygen and sulfur, by reacting carbon disulfide with a urea of the formula

(IV)

in the presence of an alakli metal base selected from the hydroxides and carbonates of sodium and potassium, in an amount of 3 moles of carbon disulfide to 1 mole of urea and 1 mole of said base, at a temperature within the range of 20° to 50° C. for 5 to 6 hours;

(b) neutralizing a compound of the formula

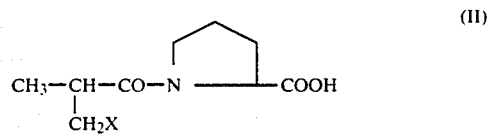
(II)

wherein X is selected from chlorine and bromine, with a basic compound selected from sodium hydrogen carbonate, potassium hydrogen carbonate, sodium carbonate, potassium carbonate, sodium hydroxide, potassium hydroxide, triethylamine and pyridine, in an amount of 2 moles basic compound to 3 moles of the compound of formula (II);

(c) mixing the neutralized compound from step (b) with the solution from step (a) in an amount of 1 to 4 moles of compound of formula (III) to 1 mole of compound of formula (II);

(d) heating the mixture from step (c) at a temperature within the range of 30° to 100° C. for 4 to 5 hours so as to displace the halogen from the compound of formula (II) with the anion of formula (III); and (e) hydrolyzing the mixture from step (d) by adjusting the pH of the mixture to a pH within the range of 0.5 to 2.5 by adding an acid selected from hydrochloric, sulfuric and formic acids and by stirring the mixture for about an hour.

10. The method as claimed in claim 9 wherein step (e) includes the further step of adding acid and zinc powder in an amount of about 1 mole of compound of formula (I) to 0.5 to 1 mole of acid and 0.1–0.2 mole of zinc, wherein the acid is selected from sulfuric and hydrochloric acids.

* * * * *